United States Patent [19]

Robertson

[11] 4,344,434
[45] Aug. 17, 1982

[54] ILEOSTOMY APPLIANCE AND METHOD FOR IMPLANTING THE SAME

[75] Inventor: William G. Robertson, Santa Barbara, Calif.

[73] Assignee: Santa Barbara Medical Foundation Clinic, Santa Barbara, Calif.

[21] Appl. No.: 268,879

[22] Filed: Jun. 1, 1981

[51] Int. Cl.³ .............................................. A61F 5/44
[52] U.S. Cl. .................................... 128/283; 128/1 R
[58] Field of Search ............... 128/283, 1 R, 348–351, 128/246, 247, 736

[56] References Cited

U.S. PATENT DOCUMENTS

| | | | |
|---|---|---|---|
| 2,324,520 | 7/1943 | Lamson | 128/1 R |
| 2,510,766 | 6/1950 | Surface | 128/1 R |
| 2,564,399 | 8/1951 | Franken | 128/283 |
| 3,253,594 | 5/1966 | Matthews et al. | 128/1 R |
| 3,447,533 | 6/1969 | Spicer | 128/283 |
| 3,802,418 | 4/1974 | Clayton | 128/283 |
| 3,828,782 | 8/1974 | Polin | 128/1 R |
| 3,938,521 | 2/1976 | Ritota et al. | 128/283 |
| 3,952,726 | 4/1976 | Hennig et al. | 128/1 R |
| 4,019,499 | 4/1977 | Fitzgerald | 128/1 R |
| 4,030,500 | 6/1977 | Ronnquist | 128/283 |
| 4,117,847 | 10/1978 | Clayton | 128/283 |
| 4,121,589 | 10/1978 | McDonnell | 128/283 |
| 4,137,918 | 2/1979 | Bogert | 128/283 |
| 4,209,010 | 6/1980 | Ward et al. | 128/283 |
| 4,210,131 | 7/1980 | Perlin | 128/283 |
| 4,241,735 | 12/1980 | Chernov | 128/344 |
| 4,245,652 | 1/1981 | Kelly et al. | 128/283 |

Primary Examiner—Stephen C. Pellegrino
Assistant Examiner—T. J. Wallen
Attorney, Agent, or Firm—Daniel J. Meaney, Jr.

[57] ABSTRACT

An ileostomy appliance including a support housing having an attachment plate and elongated central member extending substantially perpendicular therefrom wherein the support housing has an aperture extending through the attachment plate and axially through the elongated central member forming a passageway therethrough with a preshaped collapsible member having a fluid-tight outer surface and an interior cavity which may be filled with a resilient foam material, being positioned around and in fluid-tight sealing engagement with the exterior surface of the elogated central member and with the preshaped collapsible member spaced a predetermined distance from the attachment plate and wherein the end of the preshaped collapsible member which is adjacent the opening of the elongated central member is attached to the opening in the preshaped collapsible member to provide an unobstructed opening of the elongated central member through the preshaped collapsible member and including means for withdrawing fluid from the interior cavity of the preshaped collapsible member to a reduced or negative pressure therein and to enable ambient atmospheric pressure to collapse said preshaped collapsible member to reduce the geometrical dimension thereof and for enabling fluid to be drawn into the interior cavity at ambient atmospheric pressure to expand the preshaped collapsible member back to its original shape and size is shown. A method for implanting an ileostomy closure and drainage appliance in a user is also shown.

20 Claims, 20 Drawing Figures

ILEOSTOMY APPLIANCE AND METHOD FOR IMPLANTING THE SAME

BACKGROUND OF THE INVENTION

1. Field of the Invention

This invention relates to an ileostomy appliance and more particularly to an ileostomy closure and drainage appliance to be worn by a user in order to provide a continent ileostomy.

2. Description of the Prior Art

The use of appliances for occluding colostomies and ileostomies in order to make the same continent is well known in the art.

A survey of methods and apparatus that are known for maintaining or obtaining a continent colostomy is described in an article entitled "The Quest for Continence: A Morphologic Survey of Approaches to a Continent Colostomy" authored by J. B. Tenny; M. Ang; and M. J. Graney, M. D., which appeared in the October, 1978 issue, Volume 21, No. 7 at pages 522 to 534, inclusive, of the *American Society of Colon and Rectal Surgeons Review*, generally referred to as the "Dis. Col. & Rec." publication. The above article relating to "The Quest for Continence" disclosed a survey of methods including mechanical occluders (without covers) which utilized surgical methods and apparatus including the use of an inflatable "cuff" that acted as an occluding balloon to seal the colon.

The use of an inflatable balloon to obtain artificial control of the anal colostomy in sheep is set forth in an article entitled "Artificial Control of the Anal Colostomy in Sheep" prepared by Theodore H. Stanley, M. D.; Thomas R. Kessler; La Ree Wiseman; and Charles A. Blumle, A. B., which was published in April, 1969, Volume 9, No. 4, at pages 223 to 227, inclusive, of the *Journal of Surgical Research*. In the artificial control of the colostomy in sheep described in the above-referenced article, the occlusive mechanism used an implanted ring which was a thin silicone rubber tube with an expanding balloon at its tip.

The use of an inflatable air-filled balloon or bladder member in conjunction with attachment plates to form closure means for artificial body openings is well known in the art. Typical of such closure means are described in U.S. Pat. Nos. 2,564,399; 2,510,766; 3,253,594; 3,802,418; 3,447,533; 2,324,520 and in German Pat. No. DT 2,754,807 and Great Britain Pat. No. 2,007,983 A. German Pat. No. DT 2,754,807 discloses a magnetic ring and plug assembly which utilizes polyvinyl acetal foam in a hydrophobic casing.

The closure means described in U.S. Pat. No. 2,564,399 includes a base plate, a tube and means for attaching an inflatable rubber bladder to the end of the tube. The rubber bladder is adapted to have air inserted into or removed therefrom through a passageway formed by a tube extending from the base plate to the rubber bladder. In use, the closure device is inserted into an artificial rectal opening and the rubber bladder is then inflated to close or occlude the opening. A ring of hard material may be introduced in the vicinity of the rectal opening to prevent the inflated rubber bladder from being pressed out of the opening due to the pressure of the contents of the rectum.

U.S. Pat. No. 2,510,766 discloses a colostomy control device which terminates in a solid, resilient head member having a rim portion which engages the sidewall of the colostomy when it is inserted therein. The head member can be collapsed or reduced in size during insertion by means of stretching and elongating the resilient head member.

The use of a compression implant for urinary incontinence is disclosed in U.S. Pat. No. 4,019,499 and utilizes a flexible elastomeric skin formed of medical grade silicone rubber which encapsules a filler of curable resilient material such as medical grade silicone rubber, which when cured, tends to remain in place and is resiliently deformable to provide a supporting pressure for the urethra.

The use of irrigating drains for ileostomy patients is well known in the art and a disposable irrigated drain with a stoma for ileostomy patients is disclosed in U.S. Pat. No. 3,830,235.

It is also known in the art to utilize closure appliances which include a plate member and permanent magnets in order to provide a magnetic coupled closure device for an intestinal opening. Typical of such devices are those disclosed in U.S. Pat. Nos. 3,952,726; 4,205,678; and 4,210,131.

It is further known in the art to surgically form a closure for an ileostomy. Typical of such an operation is to form what is known as a KOCH POUCH in the ileal wall which functions as a drainable closure for the ileostomy.

SUMMARY OF THE PRESENT INVENTION

This invention discloses a novel, unique and improved medical device in the form of an ileostomy closure and draining appliance to be worn by a user.

In the preferred embodiment of the present invention, the ileostomy appliance includes a support housing having an attachment plate having opposed parallel surfaces and an elongated central member having a predetermined axial length extending substantially perpendicular therefrom. The support housing includes an aperture extending through the attachment plate and axially through the elongated central member. The aperture forms a passageway through the elongated central member which terminates at openings at each end thereof. A preshaped closure member having a fluid-tight, outer surface and a resilient foam filled interior cavity is positioned around and in fluid-tight sealing engagement with the exterior surface of the elongated central member. The preshaped collapsible member is positioned around the elongated central member with one end of the preshaped collapsible member spaced a predetermined distance from the attachment plate. The other end of the preshaped collapsible member is located adjacent the opening of the elongated central member. The edges of both openings in the ends of the preshaped collapsible member are attached through a fluid-tight seal to the exterior surface of the elongated central member. The opening of the elongated central member adjacent the opening end of the preshaped collapsible member is unobstructed. The preshaped collapsible member includes means for withdrawing fluid from the interior cavity and resilient foam material causing a reduced or negative pressure therein enabling ambient atmospheric pressure to collapse the preshaped collapsible member to reduce the geometric dimension thereof to permit insertion thereof into an ileostomy. In addition, the preshaped collapsible member includes means for enabling fluid to be drawn into the interior cavity of the preshaped collapsible member at ambient atmospheric pressure after the same has been inserted into the colostomy to expand the preshaped collapsible member and resilient foam material back into their original shape and into sealing engagement with the interior surface of an ileal wall of an ileostomy. A unidirectional valve such as a miter valve, may be provided in the support housing for forming a fluid-tight enclosure therefor and which is responsive to an insertion of a catheter through the attachment plate and into the elongated central member to form an opening through which the catheter can be slidably inserted into the passageway while maintaining a sealing engagement with the miter valve. When the preshaped collapsible member and resilient foam material are urged back to their original shape, a sealing engagement is made with a ring shaped sealing surface which is surgically formed by pleats in the interior of the ileal wall of the ileostomy. The sealing engagement formed between the outer surface of the preshaped collapsible member and the so-formed ring shaped sealing surface formed by the pleats provides continence for the ileostomy.

In the known prior art devices, an inflatable bladder or balloon positioned between the interior walls of an ileostomy or colostomy is usually utilized in combination with an implanted ring, magnet or other means. Such implanted ring, magnet or other means cooperates with the expanded balloon to prevent withdrawal of the expanded balloon through the opening of the colostomy or ileostomy. In addition, expansion of the balloon is accomplished by introducing air into the balloon to expand it to the desired geometrical dimension.

Thus, one disadvantage of the prior art devices is that a separate mechanical element must be utilized in combination with the expanded balloon member in order to insure a permanent sealing arrangement between the exterior of the expanded balloon member and the walls of the colostomy. Further, the balloon must be expanded to a certain dimension in order to obtain a predetermined seal for a continent ileostomy or colostomy.

One other problem associated with the prior art devices is that the amount of expansion of the expandable member is determined solely by the amount of fluid or air urged therein under pressure and the resiliency and other characteristics of the material which forms the same. Thus, during surgery, or during a period when the closure device is implanted within an opening, expansion of the balloon member to a geometrical dimension greater than that required for proper sealing in a ileostomy may result in undue pressure on the ileostomy which affects the long term permanancy of the closure device. Also, the user of the device may experience a high degree of irritation from such pressure during use of the closure device. The use of an insufflator bulb having a premeasured volume of air and permanently coupled to a balloon would have a tendency to control the volume of air to be ultimately urged into the balloon member, but the premeasured volume of air is determined by the pre-measured air in the insufflator bulb and not by the volume of air in the inflated balloon itself.

Another known disadvantage of the prior art apparatus is that a user must remove the appliance in order to irrigate the colostomy or drain the ileostomy.

Another disadvantage of the prior art apparatus and surgically formed closures for an ileostomy is that the ileostomy may develop a back pressure which may result in seepage or other disruption of the ileostomy closure.

The present invention overcomes several of the known disadvantages and problems associated with the prior art closure means and appliances. One advantage of the present invention is that the ileostomy appliance utilizes a preshaped collapsible member which includes a fluid-tight outer surface and inner cavity which is filled with a resilient foam material. The combination of the fluid-tight outer surface and the resilient foam material insures that the preshaped collapsible member can be expanded and filled with only a predetermined volume of fluid.

Another advantage of the present invention is that the ileostomy can be drained through the ileostomy appliance without the user removing the same and the ileostomy appliance can remain in the user without the necessity of removal for relatively long periods of time in the order of three months to six months or more.

A further advantage of the present invention is that the ileostomy appliance can be deflated by use of a syringe to withdraw fluid from the interior of the cavity and resilient foam material to reduce the size of the preshaped collapsible member to a size which permits insertion of the appliance into and through a ring shaped sealing surface formed by pleats in the ileal wall. Inflation is obtained by enabling fluid to be drawn back into the cavity at ambient atmospheric pressure to expand the preshaped collapsible member and resilient foam material back to their original shape with a predetermined volume of fluid.

A yet further advantage of the present invention is that a unidirectional valve can be utilized in conjunction with the ileostomy appliance to form a drainable closure which functions to maintain the ileostomy in a continent condition and wherein a catheter can be inserted through a unidirectional valve to drain the ileostomy or otherwise irrigate the same.

A still yet further advantage of the present invention is that the ileostomy device can be used in combination with a surgically formed ring shaped sealing surface thereby avoiding the necessity of implanting a rigid ring, magnetic members and the like within the body of a user.

A still yet further advantage of the present invention is that the distance between the preshaped collapsible member and an attachment plate, which is urged against the body of a user, can be selected to have a predetermined distance which is necessary to accommodate the various thickness of subcutaneous tissue of a user while forming a fluid-tight continent seal between the outer surface of the preshaped collapsible member and a ring shaped sealing surface formed by pleats while urging the attachment plate against the body of a user thereby insuring a positive continuous sealing arrangement between the preshaped collapsible member and the pleated ring shaped sealing surface to form a continent ileostomy.

A BRIEF DESCRIPTION OF THE DRAWING

The foregoing and other advantages of this invention will become apparent from the following description of the preferred embodiment when considered together with the illustrations in the accompanying drawing which includes the following figures.

DESCRIPTION OF THE PREFERRED EMBODIMENT

Figures 1, 5:
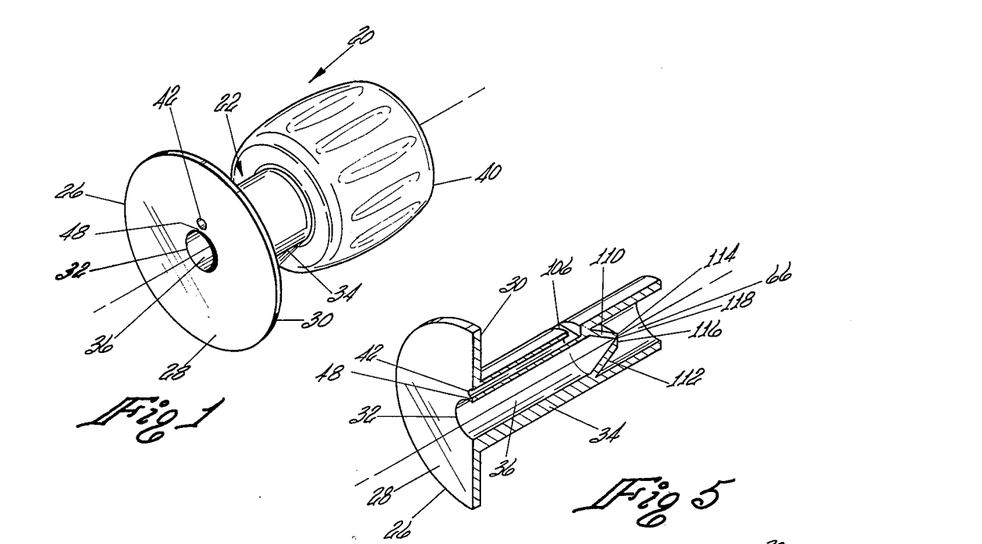
FIG. 1 is a perspective view of an ileostomy appliance of the present invention.
FIG. 5 is a isometric view partially in cross section of the support housing showing the relationship between the passageway and fluid tube located within the interior of the elongated central member.

The ileostomy appliance shown generally by arrow 20 is adapted to be used as a closure and draining appliance to be worn by a user. The ileostomy appliance 20 includes a support housing 22 which includes a planar attachment means 26 which, in the preferred embodiment, is an attached plate, having two opposite faces 28 and 30. The planar attachment means includes an opening 32 extending therethrough and into communication with the end of the elongated central member 34 and which defines a passageway 36 in the interior of the elongated central member 34. Face 30 of the planar attachment means 26 is adapted to engage the body of a user.

The elongated central member 34 has a predetermined axial length which is determined by the distance between the opening of the ileostomy in a user and the distance that the ring shaped sealing surface formed by the pleats or other element is adapted to be located within the interior of the ileostomy wall. The elongated central member 34 has an aperture extending through the center thereof which defines an opening at each end thereof. This is shown in greater detail in FIG. 6. The elongated central member 34 has one end thereof attached to the body engaging face 30 of the planar attachment means 26. The opening of the one end of the passageway 36 within the interior of the elongated central member 34 communicates with the opening 32 and extends through the planar attachment means 26.

In the preferred embodiment, a means defining a preshaped collapsible member 40 is located at the end of the elongated central member 34 which is opposite to the end which communicates with the opening 32 of the planar attachment means 26.

A fluid tube 42 extends through the planar attachment means 26. In the preferred embodiment, fluid tube 32 is located within the interior of the elongated central member 34. The fluid tube 42 extends into the preshaped collapsible member 40. The fluid tube 42 is provided as a means for withdrawing fluid from and enabling fluid to be drawn into the interior cavity and resilient foam material of the preshaped collapsible member 40. The preshaped collapsible member 40 is affixed through a fluid-tight seal to the exterior of the elongated central member 34. The fluid tube 42 terminates in an aperture 48 which is adapted to receive a syringe shown as syringe 162 in FIG. 11. In the preferred embodiment, a syringe is used to withdraw fluid from the interior cavity of the preshaped collapsible member 40. Thereafter the syringe may be used to enable fluid to be drawn back into the interior cavity of the preshaped collapsible member 40 to expand the same back to its original shape. However, since a reduced or negative pressure is present, fluid, such as air, may be drawn back into the preshaped collapsible member 40 without a syringe.

A unidirectional valve such as a miter valve, is located past the opening 32 of the planar attachment means 26 (shown in detail in FIGS. 5 and 6) enabling the means defining the flexible sealing members thereof to be located within the interior of the elongated central member 34. FIGS. 2 through 5 inclusive, show in greater detail the relationship between the various elements which form the ileostomy closure and draining appliance.

Figure 2:
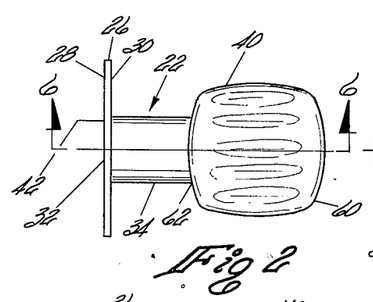
FIG. 2 is a front plan view of an ileostomy appliance of the present invention.
Figure 3:
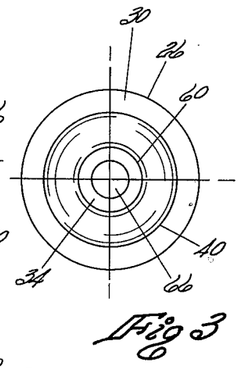
FIG. 3 is a right end plan view of the ileostomy appliance of FIG. 2.

FIGS. 2 and 3 show the construction of the preshaped collapsible member which, in a preferred embodiment, is a fluid-tight, deflatable toroidal shaped member 40. In FIG. 2, the toroidal shaped member 40 includes means defining a pair of spaced opposed openings 60 and 62 which are axially aligned with the axis of the toroidal shaped member 40. Openings 60 and 62 extend from the exterior of the toroidal shaped member to the surface thereof. In addition, each of the coaxially aligned openings 60 and 62 communicate with the interior cavity of the toroidal shaped member 40 and are attached, through a fluid-tight seal, to the exterior of the elongated central member 34. The fluid tube 42 extends through the planar attachment means 26 as noted above.

FIG. 3 illustrates that the opening 60 in the preshaped collapsible member 40 is fixed in sealing engagement with opening 66 of the elongated central member 34. The face 30 of the planar attachment means 26 which engages the skin of a user is shown.

Figure 4:
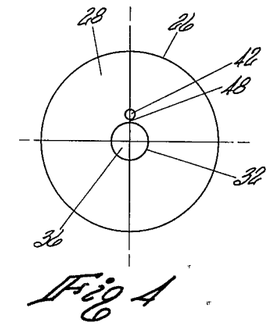
FIG. 4 is a left end plan view of the ileostomy appliance of FIG. 2.

FIG. 4 illustrates the passageway 36 which communicates with the opening 32 extending through the planar attachment means 26 and that the fluid tube 42 communicates with an opening 48 located in face 28 and which extends through the planar attachment means 26.

FIG. 5 is an isometric view, partially in cross-section, which illustrates the construction details of an integral member having the planar attachment means 26, the elongated central member 34, the passageway 36, the fluid tube 42, a fluid inlet 106 and the miter valve having flexible sealing members 110 and 112. The opposed faces 28 and 30 of the planar defining means are formed to be annular in shape in the preferred embodiment. Opening 32 and aperture 48 are formed in the planar attachment means 26 and communicate with passageway 36 and fluid tube 48, respectively. In the preferred embodiment, the elongated axis of the fluid tube 42 is substantially parallel to that of the elongated axis of passageway 36 and the fluid tube 42 is spaced from the passageway 36.

In construction, the thickness of the exterior outer surface of the elongated central member 34 which extends from the planar surface 30 to about the fluid inlet 106 has sufficient thickness to accommodate the fluid tube 48. However, the remaining portion of the exterior outer surface extending from about the fluid inlet 106 to the opening 66 has a thickness which is substantially less than that portion of the exterior outer surface having the fluid tube 42 formed therein. The difference in thickness is about equal to the thickness of the flexible sealing members 110 and 112 such that when a catheter having a diameter which is slightly less than the diameter of opening 32 is inserted into passageway 36, that catheter engages and urges the flexible sealing members 110 and 112 against the exterior outer surface of the elongated central member 34 such that lips 114 and 116 separate enabling an opening 118 formed between the lips 114 and 116 to have a diameter sufficient to pass a catheter. This is shown in detail in FIG. 14.

It is envisioned that the fluid tube 42 could be a separate elongated tube which extends along the outside of the exterior outer surface of the elongated central member 34 between aperture 48 and the fluid inlet 106 or other appropriate orifice.

Figure 6:
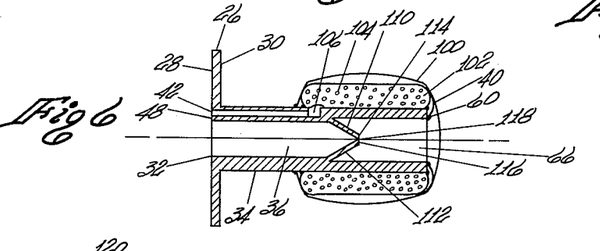
FIG. 6 is a cross section view taken along section lines 6—6 of FIG. 2.

FIG. 6 shows in greater detail the construction of the elongated central member 34 having the means for defining the fluid tight, deflatable toroidal shaped member 40 mounted thereon and the relationship therebetween to the unidirectional valve defined by flexible sealing members 110 and 112.

Figures 10, 11, 12:
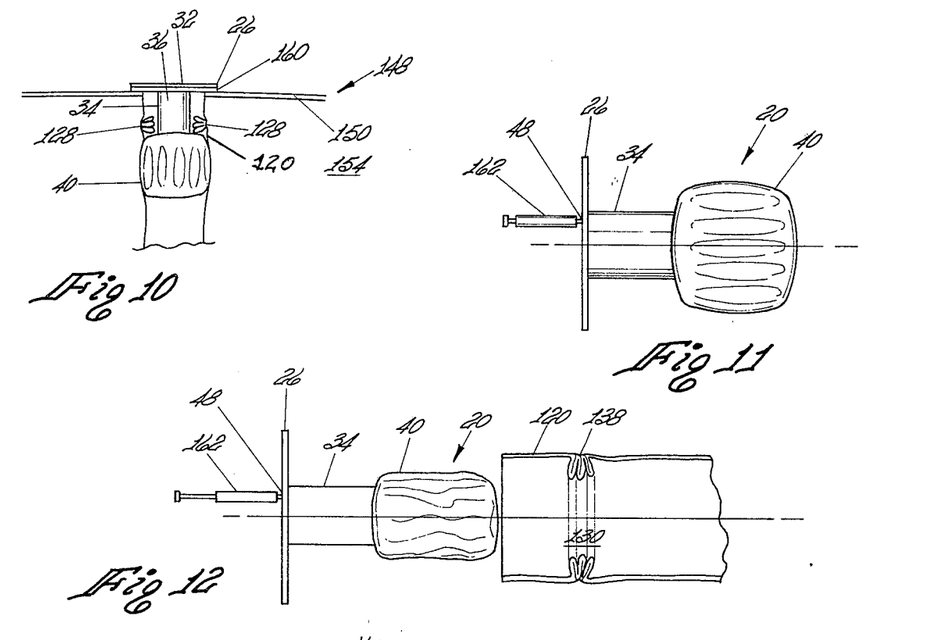
FIG. 10 is a pictorial representation of an enclosure device implanted within an ileostomy having a ring shaped sealing surface formed by pleats.
FIGS. 11, 12 and 13 are a series of views showing the steps for insertion of an ileostomy appliance into an ileostomy having the ring shaped sealing surface formed by pleats formed in the ileal interior wall.

In FIG. 6, the planar attachment means 26 has the opening 32 which extends through the two opposite faces 28 and 30 shown communicating with the one end of the elongated central member 34 and the passageway 36 which extends axially therethrough. Thus, the passageway 36 extends from opening 32, through a miter valve defined by flexible members 110 and 112 and out the other end of opening 66 of the elongated central member 34 which has the axially aligned opening 66 attached thereto. The elongated central member 34 has a predetermined axial length which is determined by the distance between the planar attachment means 26, located against the body of a user, and the location of a ring shaped sealing surface formed by the pleats located in the ileal wall of the ileostomy as illustrated in FIG. 10.

The means defining a fluid-tight deflatable toroidal shaped member 40 include a fluid tight expansion resistant membrane 100 which forms the outer surface of the toroidal shaped member 40. The toroidal shaped member 40 includes a hollowed-out central area 102 which is adapted to enclose a volume of fluid. By controlling and determining the size of the hollowed-out central area 102 with the toroidal shaped member 40, the volume of fluid to be enclosed thereby can be precisely controlled.

The means for defining the toroidal shaped member 40 include means for defining the pair of spaced opposed openings 60 and 62 which are in axial alignment with the axis of the toroidal shaped member 40 and which are concurrently axially aligned with the openings of the elongated central member 34. Each of the openings 60 and 62 are in communication with the hollowed-out area 102. Opening 62 is attached to the exterior of the elongated central member 34 through a fluid-tight seal. Likewise, the opening 60 is attached to the exterior outer surface of the elongated central member 34 as noted hereinbefore.

The combination of the toroidal shaped member 40 and the exterior outer surface of the elongated central member 34 define a cylindrically shaped chamber within the hollowed-out central area 102 which likewise has a predetermined volume. A resilient foam material 104 is positioned in and substantially fills the cylindrically shaped chamber. The function of the resilient foam material is twofold; namely, (i) to trap and withhold fluid in the cellular voids formed therein; and (ii) to provide sufficient resilience and a storage means for fluid and to have sufficient resilience to help expand the membrane 100 back to its original preformed shape. The membrane 100 and the resilient foam material 104 together form a cylindrically shaped chamber which is adapted to receive a predetermined volume of fluid. Thus, once the cylindrically shaped chamber has been filled with a predetermined volume of fluid, the membrane 100 is not capable of expanding beyond the predetermined volume due to the membrane being selected of a material which resists expanding due to a fluid pressure.

The fluid tube 42 extends from the outer face 28 of the planar attachment means 26 through the exterior outer surface of the elongated central member 34, through the membrane 100 and into the fluid inlet 106 which communicates with the hollowed-out central area 102. The combination of the aperture 48, fluid tube 42, and a fluid control means which is adapted to control the withdrawal of fluid from and the application of fluid to the hollowed-out central area 102 and resilient foam means 104 is utilized to control deflation and inflation of the preshaped collapsible member 40. In the preferred embodiment, the fluid control means is a syringe. The fluid control means forms a means which is adapted for removing fluid from the resilient foam material 104 and the cylindrically shaped chamber within the hollowed-out central area 102 to establish a vacuum, reduced or negative pressure therein which enables the ambient atmospheric pressure to collapse or implode the toroidal shaped member 40 and resilient foam material 104 to reduce the exterior geometrical dimension thereof. Also, the same fluid control means can be utilized for enabling the fluid to pass through the fluid tube 42 into the cylindrically shaped chamber through the fluid inlet 106. The fluid is absorbed by the resilient foam material 104 and expands the toroidal shaped member 40 and resilient foam material 104 back to its original shape. In the preferred embodiment, the membrane 100 is formed of a material which is adapted to limit the expansion of the toroidal shaped member 40 to insure that only a predetermined volume of fluid is maintained within the cylindrically shaped chamber of the hollowed-out area 102 and resilient foam material 104 which fills the cavity. In the preferred embodiment the fluid is air. However any appropriate fluid other than air may be utilized.

In the preferred embodiment, the unidirectional valve or miter valve comprises flexible members 110 and 112 which include lips 114 and 116, the edges of which define an opening 118. The unidirectional valve formed by flexible members 110 and 112 terminates in flexible lips 114 and 116, respectively, which are in engagement with each other to form a fluid-tight closure for the elongated central member 34.

Figure 14:
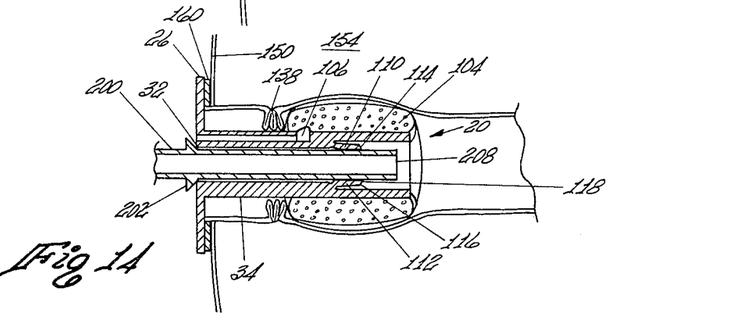
FIG. 14 is a pictorial representation partially in cross section, showing the insertion of a catheter into the ileostomy appliance.

The miter valve is adapted to cooperate with a catheter such that when a catheter is inserted therethrough and into engagement therewith, the lips 114 and 116 respond thereto to expand the opening 118 to permit a catheter to be further inserted into the passageway within the elongated central member 34 with the lips 114 and 116 maintaining sealing engagement with the exterior of the catheter which relationship is shown in FIG. 14.

Figure 7:
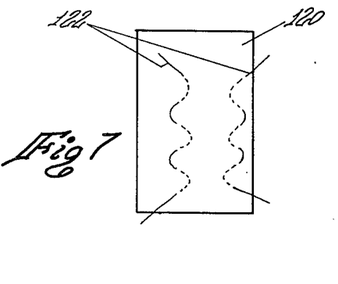
FIGS. 7, 8 and 9 illustrate a method for surgically forming a ring shaped sealing surface in an ileostomy.
Figure 8:
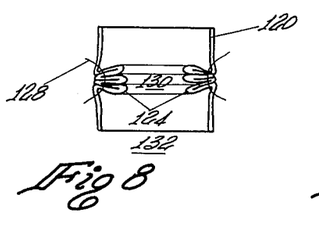
Figure 9:
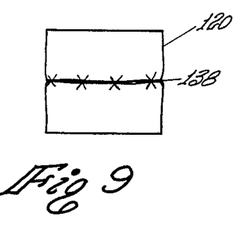

FIGS. 7, 8 and 9 illustrate a method for surgically forming a ring shaped sealing surface within the ileal wall of an ileostomy 120.

As illustrated in FIG. 7, the exterior of the ileal wall of the ileostomy 120 may be excoriated in a manner to scarify the surface as shown by lines 122, which surface is then adapted to be folded into engagement with an adjacent portion of the ileostomy 120 to form a plurality of pleats therein which defines a ring shaped sealing surface.

FIG. 8 illustrates the next surgical steps after scarifying the ileal wall of the ileostomy 120 wherein pleats are formed within the ileal wall of the ileostomy 120 to form the ring shaped sealing surface. The pleats forming the ring shaped sealing surface 124 are sutured using surgical thread 128. When the pleats are formed into a ring shaped sealing surface 124 by the suturing thread 128, an opening 130 is formed therein which has a geometrical dimension which is less than that of the normal opening 132.

FIG. 9 illustrates that the pleating is completed within the ileostomy 120 by the sutured area 138.

FIG. 10 illustrates pictorially implantation of the ileostomy appliance 20 within a user.

Typically, the body of the user shown generally as 148 has the planar attachment means 26 against the skin 150. In use, any adhesive sealing means 160 may be placed between face 30 and skin 150. The fatty or subcutaneous tissue 154 is located between the skin 150 and the fascia. The ileal wall 120 is shown to have the ring shaped sealing surface 128 formed therein by the pleats. The appliance 20 is implanted within the ileostomy 120 such that the preshaped collapsible member 40 is located below the ring shaped sealing surface 128 formed by the pleats.

As illustrated in FIG. 10, the preshaped collapsible member 40 has been expanded back into its original shape to form a sealing engagement with the ring shaped sealing surface 128 formed by the pleats. The elongated central member 34 has the passageway 36 extending axially through which communicates with opening 32 and preshaped collapsible member 40.

Figure 13:
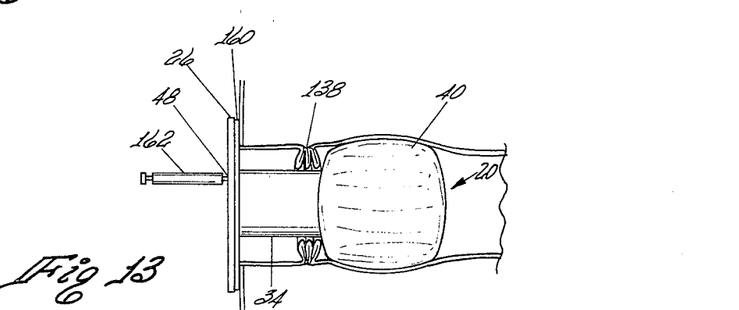

FIGS. 11, 12 and 13 illustrate diagrammatically the method for installing the ileostomy appliance in a user. The method requires the steps of surgically forming pleats in the interior of the ileostomy in the ileal wall adjacent the end which passes through the user's body forming a ring shaped sealing surface 128 and having an opening 130 therein as illustrated in FIG. 8. The cross sectional area of opening 130 is less than that of the normal opening 132 within the interior of the ileostomy.

As illustrated in FIG. 11, the ileostomy appliance 20 has the fluid tube 42 connected through aperture 48 to syringe 162. The syringe 162 is utilized to withdraw the fluid, which in the preferred embodiment is air, from the interior chamber and resilient foam material 104 (FIG. 6) of the preshaped collapsible member 40.

After the above step of deflating the preshaped collapsible member 40, the next step illustrated in FIG. 12 is the step of implanting the ileostomy device 20 within the ileostomy by inserting and passing the preshaped collapsible member 40 in its deflated condition, into and within the ileostomy and positioning the same slightly beyond the ring shaped sealing surface 128 formed by the pleats and through the opening 130 which concurrently positions the attachment plate 26 against the skin of a user.

After the ileostomy device 20 is inserted within the ileostomy past the ring shaped sealing surface 128 formed by the pleats, the next step illustrated in FIG. 13 is that of enabling a predetermined volume of fluid at ambient atmospheric pressure to be withdrawn back into the interior cavity and resilient foam material of the preshaped collapsible member 40 to expand the same back into its predetermined shape with a predetermined volume of fluid located therein. The so expanded preshaped collapsible member 40 exerts a clamping force against the edge of the ring shaped sealing surface 120 formed by the pleats of the ileostomy and urges the planar attachment means 26 against the surface of skin 150 of the user to form a fluid-tight seal between the periphery of the preshaped collapsible member 40 and the ring shaped sealing surface formed by the pleats 128 urging the planar attachment means 26 tightly against the skin 150. Of course an adhesive wafer 160 may be installed between the planar attachment means 26 and skin 150.

FIG. 14 illustrates in greater detail the insertion of a catheter 200 having a conical shaped stop member 202 formed therein which communicates with opening 32. The catheter 200 extends through flexible resilient members 110 and 112 such that the lips 114 and 116 thereof are urged apart to permit the opening 118 to pass the catheter 200 with the lips 114 and 116 in sealing engagement thereagainst. The axial length of catheter 200 between the stop member 102 and 208 is selected such that end 208 is located within the interior passageway 36 slightly away from the opening 66 of the elongated central member 34.

The remaining elements in FIG. 14 are identified with the numerals of FIG. 6 to show the relationship therebetween with the catheter 200 in its inserted position.

Figure 15:
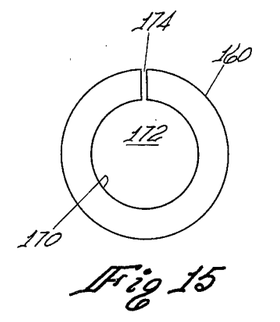
FIG. 15 is a front plan view of an adhesive seal which is adapted to be located between the attachment plate and the skin of a user.

FIG. 15 shows a typical construction of an adhesive wafer 160 having an aperture 172 formed therein which defines an edge 170 which engages the exterior outer surface of the elongated central member 34 as shown in FIG. 14. A slot 174 is provided to enable a user to remove and install the adhesive wafer 160. In the preferred embodiment, the adhesive wafer 160 may be a peristomal covering such as, for example, Stomahesive covering manufactured by Squibb. The adhesive wafer 160 heats to body temperature and becomes tacky.

Figure 16:
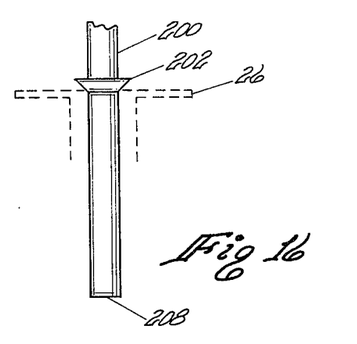
FIG. 16 is a pictorial representation of a catheter having a conical ring shaped stop member which slidably engages the opening to the attachment plate to limit travel of the catheter inserted into the opening.

FIG. 16 illustrates that the opening 32 in the planar attachment means 26 cooperates with the conical shaped stop member 202 of catheter 200 such that the end 200 extends a predetermined distance within the ileostomy appliance.

Figures 17, 18, 19, 20:
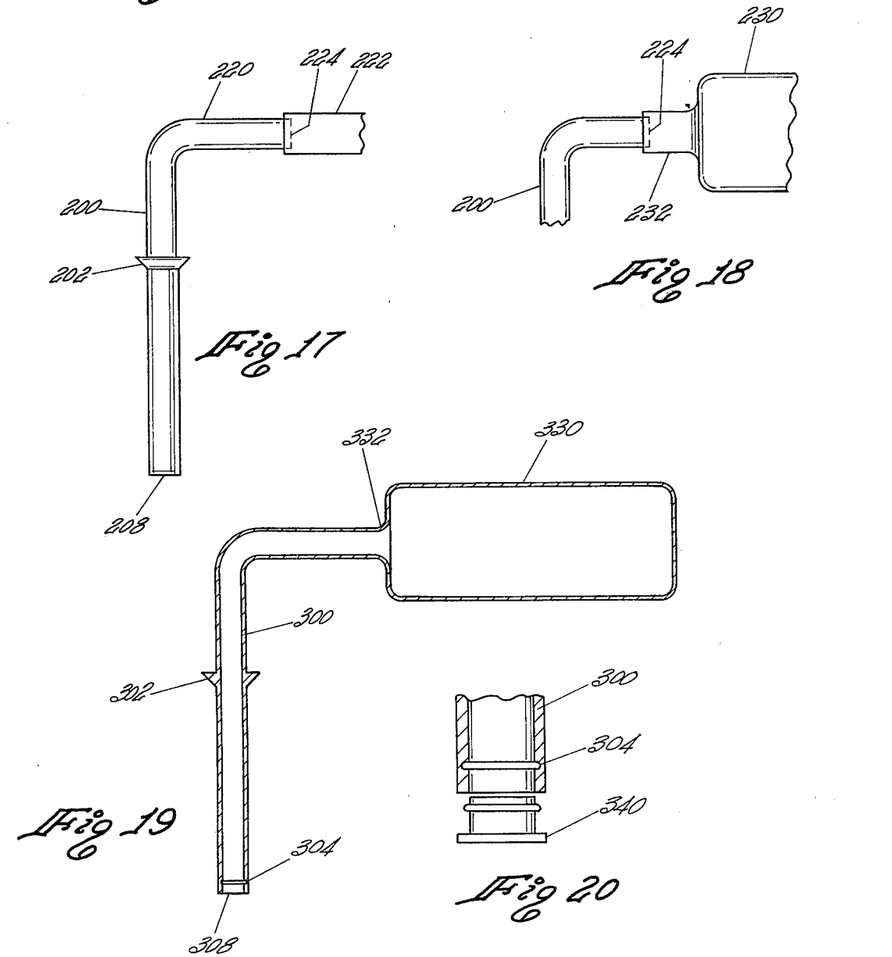
FIG. 17 is a pictorial representation of a catheter having a conical ring-shaped stop member which has a drainage tube removably attached to the end thereof.
FIG. 18 is a pictorial representation of a catheter having a conical ring shaped stop member which has a collection reservoir removably attached to the end thereof.
FIG. 19 is a pictorial representation of a disposable catheter wherein the catheter has a conical ring shaped stop member and has a collection reservoir integral therewith.
FIG. 20 is a sealing ring which is adapted to be used for sealing the inserted end of the disposable catheter of FIG. 19.

FIGS. 17 and 18 illustrate a permanent or reuseable catheter 200 which may be formed of stainless steel.

The conical shaped stop member 202 is positioned around the periphery of the catheter 200 at a preselected axial distance from one end 208 thereof. The other end of the catheter 200 may be deflated at an angle, for example 90°, with Section 220 thereof terminating in end 224. In FIG. 17, Section 220 of catheter 200 is adapted to have a drain tube 222 removeably attached thereto to enclose end 224 and to enable fluid to be drained from the ileostomy appliance, through the catheter 200 and through drain tube 222.

As shown in FIG. 18, a fluid collecting member 230 may be removeably attached through an inlet neck 232 to section 220 such that end 224 discharges the fluid from the illeostomy into the fluid collecting member 230.

FIG. 19 illustrates a disposable catheter fluid collecting member assembly. A catheter 300 has a conical shaped stop member 302 formed around the periphery thereof a predetermined axial distance from end 308. A sealing ring 304 may be located in a groove in the interior of the catheter 300. The other end of catheter 300 is fixedly attached to a fluid collecting member 330. In use, when the ileostomy is drained, the catheter-fluid collecting member assembly may be sealed by a cap 340 illustrated in FIG. 20 and then disposed of in a sealed condition. FIG. 20 shows that the cap 340 has an elongated base which makes a fluid tight sealing engagement with the ring 304 of catheter 300.

In designing the ileostomy appliance, catheter and related components, it is essential that the internal inside diameter of the catheter be of sufficient size to permit drainage. An inside diameter of about 1.0 cm is the minimum diameter for a workable ileostomy appliance.

In the preferred embodiment, the toroidal shaped member is formed of a membrane which may be a non-biodegradable plastic such as silastic. The foam material, in the preferred embodiment is a foam, one example of which is polyurethane foam.

The support housing, flange and unidirectional valve may be formed of a non-biodegradable plastic material such as silastic.

In use, the ileostomy appliance can be utilized for making an ileostomy continent. In addition, the ileostomy appliance permits the user to irrigate the ileostomy in order to obtain the maximum comfort. The sealing engagement between the preshaped collapsible member 40 and the ring shaped sealing surface 128 formed by the pleats functions as a continent closure for the ileostomy. Insertion and removal of a catheter affords the user with means for draining the ileostomy and for depositing the same in a fluid collecting bag which may be coupled to the catheter 200.

The ileostomy closure and drainage appliance has been successfully implanted in dogs in a series of controlled dog studies. In its preferred embodiment, the ileostomy appliance is designed primarily for use in human bodies.

What is claimed is:

1. An ileostomy appliance comprising
    a support housing including an elongated central member having a predetermined axial length and which communicates with an attachment plate having opposed parallel surfaces, said support housing having an aperture extending axially therethrough forming a passageway which terminates in a first opening adjacent said attachment plate and a second opening which terminates at the remote end of the elongated central member;
    a preshaped collapsible member having a fluid tight, outer surface, two ends and an interior cavity, said preshaped collapsible member being positioned around said elongated central member with the ends of the preshaped, collapsible member in fluid tight sealing engagement with the exterior outer surface of said elongated central member with one end of the preshaped collapsible member being spaced a predetermined distance from the end of the elongated central member adjacent the attachment plate and the other end of which is adjacent the second opening of the elongated central member; and
    means for withdrawing fluid from the interior cavity of said preshaped collapsible member to create a reduced pressure therein enabling ambient atmosphere pressure to collapse said collapsible member to reduce the geometrical dimension thereof and for enabling fluid to be drawn into the interior cavity of a deflated preshaped collapsible member at ambient atmospheric pressure to expand said preshaped collapsible member back to its original shape.

2. The ileostomy appliance of claim 1 further comprising
    a resilient foam material positioned within the interior cavity of said preshaped collapsible member and being responsive to said fluid being withdrawn therefrom by collapsing with said preshaped collapsible member and being responsive to fluid being drawn into the interior cavity of a deflated preshaped collapsible member to urge the same and the resilient foam material back to their original shape.

3. The ileostomy appliance of claim 2 wherein said resilient foam material is formed of a non-biodegradable material.

4. The ileostomy appliance of claim 3 wherein said resilient foam material is polyurethene.

5. The ileostomy appliance of claim 2 wherein said resilient foam filled interior cavity of said preshaped collapsible member has a predetermined volume which is capable of holding a predetermined volume of fluid therein at ambient atmospheric pressure and temperature.

6. The ileostomy appliance of claim 2 further comprising
    an adhesive wafer positioned between said planar attachment means and skin of a user.

7. The ileostomy appliance of claim 2 further comprising
    a catheter having an insertible end, and an outlet end and a conical shaped stop member formed around the periphery thereof, and spaced a predetermined distance from the insertable end.

8. the ileostomy appliance of claim 7 further comprising a fluid collecting means operatively coupled to said outer end of said catheter.

9. The ileostomy appliance of claim 7 further comprising a fluid drainage tube operatively coupled to said outlet end of said catheter.

10. The ileostomy appliance of claim 1 further comprising
    unidirectional valve having flexible sealing members positioned in said support housing for forming a fluid tight enclosure therefor and which is responsive to insertion of a catheter through the attachment plate and into the elongated central member into contact with said flexible sealing members to form an opening therein through which a catheter can be further inserted into said passageway with said flexible sealing members slidably engaging the exterior surface of a said catheter.

11. The ileostomy appliance of claim 10 wherein said means for withdrawing fluid from and enabling fluid to be drawn back into the resilient foam filled interior cavity includes
a fluid tube located in the interior outer surface of said elongated central member and extending from said preshaped collapsible member through both surfaces of said attachment plate, said fluid tube having one end thereof terminating within a fluid inlet of said interior cavity and the other end thereof which extends to at least the other surface of said attachment plate.

12. The ileostomy appliance of claim 10 wherein the ends of the flexible sealing members of said unidirectional valve are located remotely from the attachment plate and wherein each of the flexible sealing members terminate in flexible lip which is normally biased to maintain the edge thereof in engagement with each other edge thereof to form a fluid tight seal therebetween and which are responsive to a said catheter being inserted therebetween which overrides the bias and separates the edges of the flexible lips to form an opening therein and through which a said catheter can be inserted with the edges of the flexible lips forming a fluid-tight sliding sealing engagement with the exterior outer surface of a said catheter.

13. The ileostomy appliance of claim 1 wherein said preshaped collapsible member is preformed into a toroidal shaped member having opposed axially aligned openings extending therethrough from the interior cavity thereof, each of said openings being affixed through a fluid-tight seal to the exterior surface of said elongated central member.

14. The ileostomy appliance of claim 1 wherein said support housing is formed of a non-biodegradable plastic material.

15. The ileostomy appliance of claim 1 wherein said preshaped collapsible member is formed of a non-biodegradable material.

16. An ileostomy closure and drainage appliance to be worn by a user comprising
planar attachment means having two opposite faces and an opening extending therethrough, one of said faces being adapted to engage the body of a user;
an elongated central member having a predetermined axial length and having an aperture extending therethrough which defines an opening at each end thereof, said elongated central member having one end thereof attached to said body engaging face of the planar attachment means with the opening of said one end of said elongated central member communicating with the opening extending through said planar attachment means;
means defining a fluid-tight, deflatable toroidal shaped member having a hollowed-out central area adapted to receive fluid, said means for defining said toroidal shaped member including means defining a pair of spaced, opposed openings which are axially aligned with the axis of the toroidal shaped member and wherein each of said axially aligned openings extend from the exterior of toroidal shaped member into communication with said hollowed-out central area, said means defining said toroidal shaped member being positioned with the said elongated central member having its other end extending through one of said two axially aligned openings into and through said hollowed-out central area and into fluid-tight sealing engagement with the other opening of said two axially aligned openings, said one of the two axially aligned openings being positioned on the exterior of said elongated central member a preselected distance from said planar attachment means, said means defining said toroidal shaped member and said elongated central member forming a fluid-tight, cylindrically shaped chamber having a predetermined volume, within the hollowed-out central area of the means defining said toroidal shaped member, said elongated central member having said passageway extending axially through the elongated central member from the other of said faces of said planar attachment means through said hollowed-out central area to the other end of said elongated central member;
a resilient foam material positioned in and substantially filling said cylindrically shaped chamber; and
means including a fluid tube extending from the face of and through said planar attachment means and through said toroidal shaped member into communication with the hollowed-out central area for withdrawing fluid from the cylindrically shaped chamber and resilient foam material to establish a negative pressure therein enabling the ambient air pressure to collapse the toroidal shaped member and compress the resilient foam material and for enabling fluid to be drawn into the cylindrically shaped area to expand the toroidal shaped member and resilient foam material back to its original shape.

17. The ileostomy appliance of claim 16 further comprising
a unidirectional valve extending from the other face of said planar attachment means and through the opening extending therethrough into said elongated central member for forming a fluid-tight enclosure within the passageway, said valve being responsive to a catheter being inserted through the opening in the planar attachment means and into the passageway and in contact therewith to form an opening therein to permit a said catheter to be further inserted into the passageway past the unidirectional valve.

18. A method for installing an ileostomy appliance in a user comprising the steps of
surgically forming a plurality of pleats in the ileal wall of an ileostomy adjacent an end thereof which passes through an opening in the user's body, said pleats forming a ring shaped sealing surface having an opening therein of a geometrical dimension which is less than that of the ileostomy;
deflating a preshaped collapsible member by withdrawing fluid from the cavity to form a negative pressure therein which enables ambient atmospheric pressure to collapse the preshaped collapsible member to a geometrical dimension which is less than that of the ring shaped sealing surface formed by the pleats within the interior ileal wall of the ileostomy;
implanting the ileostomy device within the ileostomy by passing the preshaped collapsible member through and slightly beyond the ring shaped sealing surface formed by the pleats enabling an elongated central member which extends from the preshaped collapsible member to cooperate to position an attachment plate operatively coupled to the elongated central member against the skin of a user; and enabling a predetermined volume of fluid to be drawn back into the cavity of said preshaped collapsible member to expand the same to its predetermined shape with a predetermined volume of fluid to exert a clamping force against the edge of the ring shaped sealing surface formed by the pleats which, in turn, draws the elongated central member further into the ileostomy and concurrently urges the attachment plate against the surface of a user forming a fluid-tight seal between the exterior surface of the preshaped collapsible member and the ring shaped sealing surface formed by the pleats to occlude the ileostomy of a user.

19. The method of claim 18 wherein said preshaped collapsible member has its cavity filled with a resilient foam material and wherein the step of deflating said preshaped collapsible member includes withdrawing fluid from the cavity and resilient foam material and the step of enabling a predetermined volume of fluid to be drawn into the cavity includes enabling said fluid to be drawn into said resilient foam material.

20. The method of claim 19 further comprising the steps of forming a closure within a passageway located interior of the elongated central member by means of a miter valve having flexible sealing members to transport fluids within the ileostomy by means of a catheter which can be inserted through the planar attachment plate into the elongated central member into engagement with the miter valve and past the flexible sealing members.

* * * * *